United States Patent [19]

Frigg

[11] Patent Number: 5,116,336
[45] Date of Patent: May 26, 1992

[54] OSTEOSYNTHETIC ANCHOR BOLT

[75] Inventor: Robert Frigg, Davos, Switzerland

[73] Assignee: Synthes (U.S.A.), Paoli, Pa.

[21] Appl. No.: 539,595

[22] Filed: Jun. 18, 1990

[30] Foreign Application Priority Data

Mar. 19, 1990 [CH] Switzerland .......... 886/90

[51] Int. Cl.⁵ .................. A61F 5/00
[52] U.S. Cl. .................. 606/65; 606/60; 606/61; 606/66; 606/73
[58] Field of Search .......... 606/60, 61, 65, 66, 606/53, 73

[56] References Cited

U.S. PATENT DOCUMENTS

| | | | |
|---|---|---|---|
| 3,990,438 | 11/1976 | Pritchard | 606/65 X |
| 3,996,931 | 12/1976 | Callender, Jr. | 606/65 |
| 4,530,114 | 7/1985 | Tepic | 606/60 X |
| 4,621,629 | 11/1986 | Koeneman | 606/65 |
| 4,640,271 | 2/1987 | Lower | 606/65 |
| 4,716,893 | 1/1988 | Fischer et al. | 606/65 |
| 4,858,601 | 8/1989 | Glisson | 606/65 X |

Primary Examiner—Robert A. Hafer
Assistant Examiner—Kerry Owens
Attorney, Agent, or Firm—Davis, Hoxie, Faithfull & Hapgood

[57] ABSTRACT

An osteosynthetic anchor bolt has a shaft which has at its front end an external thread having a major diameter greater than the diameter of the shaft and at the rear an internally threaded socket to accept a compression screw. The profile of the external thread is designed in such manner that there is maximum possible resistance to axial pressures acting on the anchor bolt frontally, laterally or both.

8 Claims, 2 Drawing Sheets

OSTEOSYNTHETIC ANCHOR BOLT

FIELD OF THE INVENTION

This invention relates to an anchor bolt for use in osteosynthesis and to a hip fixation device using the novel bolt.

BACKGROUND OF THE INVENTION

In the osteosynthetic treatment of fractures of the neck of the femur, that is, fractures of the femur in which the neck connecting the head with the rest of the femur is broken, the bone fragments are connected to one another by means of a temporarily inserted fixation device. Such devices, as described, for example, in U.S. Pat. No. 4,095,591, consist essentially of:
- an anchor bolt or lag screw to be screwed into the head of the bone, and having a headless shaft with an internally threaded socket;
- a plate, to be attached to the main section or shank of the femur, with a barrel which serves to hold the shaft of the anchor bolt; and
- a compression screw to be screwed into the threaded socket of the anchor bolt shaft, and having a head which, in position, rests on the shoulder of the barrel. In the profession, these devices are known as dynamic hip screws.

The operating technique for implanting such fixation devices is described in Swiss patents CH-A5 634.741 and 634.742. In general the anchor bolt is inserted into the head of the femur, traversing the fracture. The plate is then attached to the shank of the femur with its barrel over the shaft of the bolt. The compression screw is thereupon inserted into the socket in the anchor bolt, the arrangement being such that the compression screw is retained in its position by engagement with the barrel of the compression plate so that when screwed into the anchor bolt, it retracts the bolt, reducing the fracture.

Anchor bolts used in such devices have to date had external threads whose profiles are typical of bone screws and thoroughly conventional.

Such conventional profiles create maximum resistance to tractive forces acting on the bolt, because of their approximately saw-tooth profile, which faces the end of the bolt shaft. However, in the use under discussion here, because of the ability of the anchor bolt to slide in the plate socket, only limited tractive forces act on the anchor bolt, so that the conventional profile is not appropriate. In contrast, the resistance of the conventional profiles against pressure forces that occur precisely in this use of such anchor bolts is rather limited.

A further disadvantage of the conventional screw profiles is that because of their sharp threading they offer practically no resistance to lateral pressures. Precisely such lateral forces occur, however, in the physiological load on the operated hip joint head in question. In the case of porotic femur heads, these lateral forces can lead to a penetration of the thread into the joint. The reason is that part of the spongiosa is missing, so that the bolt can be anchored only in the thin cortical skin of the femur head. In other words, only the thread tips carry the laterally occurring load on the bolt. The problem of bolt penetration into the hip joint is very relevant, and is described, for example, by A. H. R. W. Simpson et al in *British Journal of Accident Surgery*, Vol. 20, No. 4, July 1989. This article reports that in a total of 223 cases studied, 14 bolts penetrated the hip joint, and, with 12 bolts there was superior penetration of the hip head.

SUMMARY OF THE INVENTION

In accordance with the invention an anchor bolt or lag screw is provided whose external threads are shaped so that the bolt can be implanted with maximum protection for the bone. The thread design is also calculated to accommodate physiologically occurring loads in the best possible manner. These results are obtained without enlargement of the bolt which might lead to avascular head necroses.

In accordance with one aspect of the invention, an anchor bolt for osteosynthetic purposes is provided having an external thread of buttress configuration, preferably a thread whose forward facing flanks are essentially perpendicular to the axis of the bolt.

In another aspect the invention comprises a device for the fixation of fractures of the neck of the femur comprising an anchor bolt having an external thread as described and an internally threaded shaft, a plate having a barrel adapted to fit over the shaft of the anchor bolt and a compression screw adapted to engage the internal threads of the anchor bolt.

SPECIFIC DESCRIPTION OF THE DRAWINGS

The invention will be further described in connection with the drawings, in which.

DETAILED DESCRIPTION OF A PREFERRED EMBODIMENT

Figure 1:
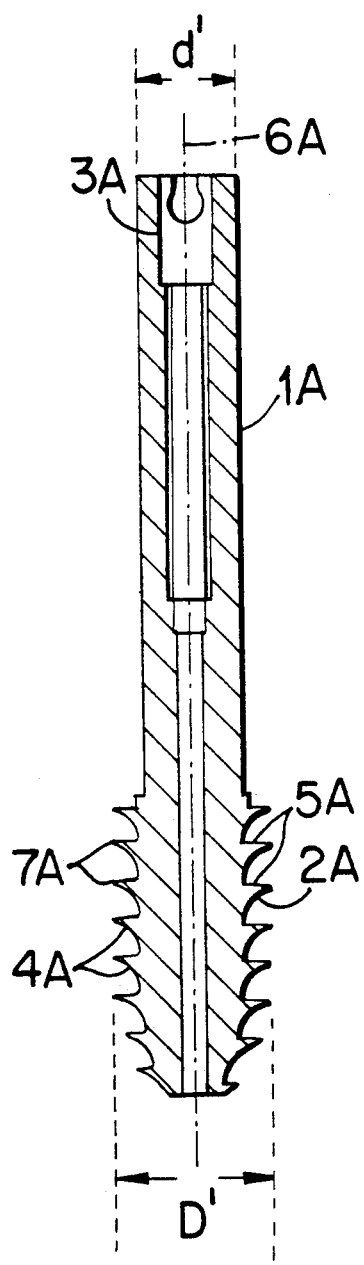
FIG. 1 shows a section through a conventional anchor bolt.

Referring to FIG. 1, an anchor bolt according to the current state of the art has a shaft 1A with a diameter d', and at the front, an external thread 2A with a major diameter D', greater than d'. At the back an internal thread 3A is provided to accept a compression screw (not illustrated). The conventional profile of external thread 2A consists of flanks 5A facing backward toward shaft 1A and perpendicular to bolt axis 6A, and concave flanks 4A facing forward toward the bolt tip. The outer edges of the threads have sharp peaks 7A. This conventional sawtooth profile offers maximum resistance to tractive forces acting on the bolt.

Figure 4:
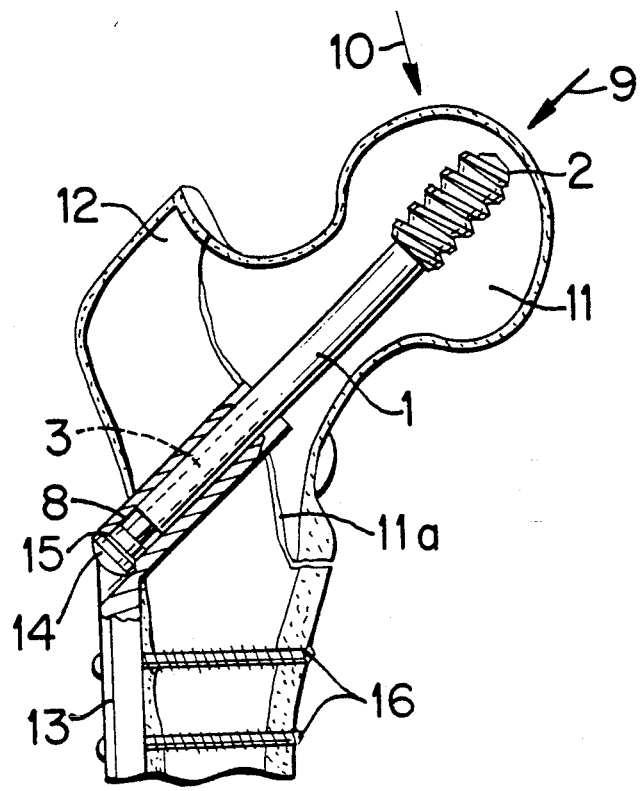
FIG. 4 shows a section through an anchor bolt according to the invention, implanted in the femur, as a component of a fixation device for setting a broken hip joint neck.

As shown in FIG. 4, in the use with which the invention is concerned, an anchor bolt is arranged movably in a plate barrel 8. Because it is possible for the anchor bolt to slide in the plate socket 8, only limited tractive forces act on the anchor bolt, and thus the conventional profile illustrated in FIG. 1 is inappropriate.

Figure 2:
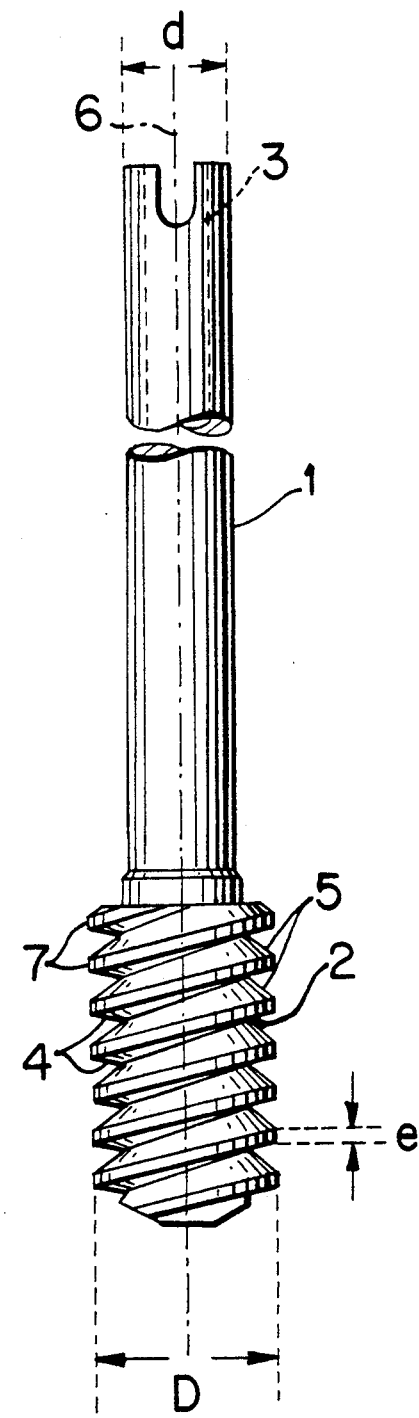
FIG. 2 shows a section through an anchor bolt according to the invention.

Referring to FIG. 2 which shows a bolt according to the invention, it comprises a shaft 1 with diameter d. At the front end of shaft 1 is an external thread 2 having a major diameter D, greater than d. A threaded socket 3 in the rear end of the shaft is provided to accept a compression screw (See FIG. 4).

Figure 3:
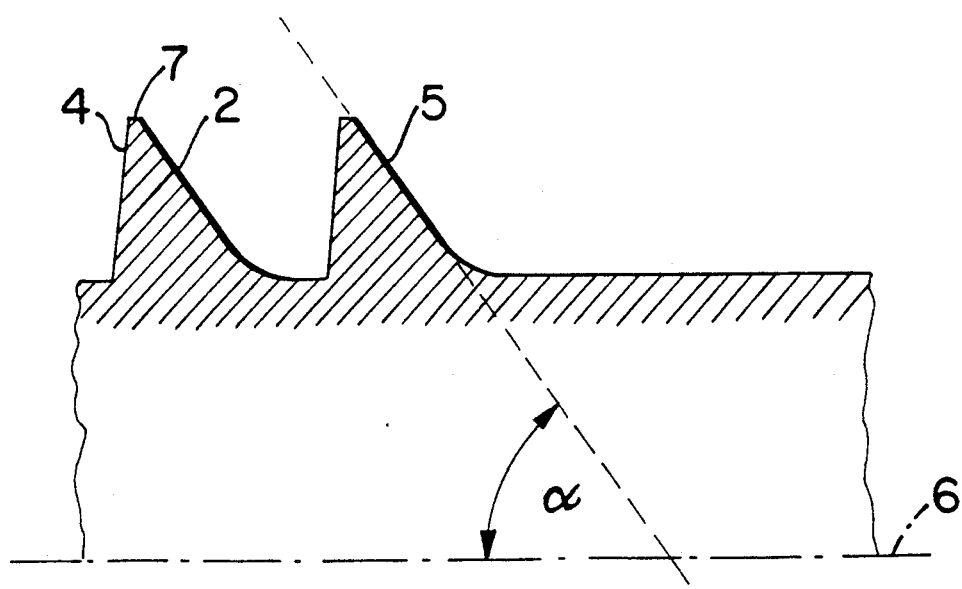
FIG. 3 shows an enlarged partial section through the profile of the anchor bolt according to FIG. 2.

In contrast to the conventional profile of external thread 2A illustrated in FIG. 1, an anchor bolt according to the invention, as shown particularly in the enlarged partial section of FIG. 3, is of buttress shape and has forward flanks 4 essentially perpendicular to the bolt axis 6. This provides maximum resistance to axial pressures acting from the front on the anchor bolt (arrow 9 in FIG. 4). The crests 7 of external thread 2 are designed with a blunted or flattened area 3, which can range between 0.5 and 1.0 mm, preferably 0.7 mm, wide, front to back. This thread design gives improved resistance to pressures acting laterally on the anchor bolt (arrow 10 in FIG. 4).

As can be seen in FIG. 3, the rearward-facing flanks 5 of external thread 2 are positioned at an angle α (with bolt axis 6) in a range of 50°–60°. Preferably, α is 55°.

FIG. 4 shows a fixation device including an anchor bolt according to the invention used for setting a fracture 11a in the head 11 of a femur 12.

As shown in FIG. 4 the anchor bolt having external thread 2 is screwed into the head of the femur. A plate 13 is attached to the main segment or shank of the femur 12 by means of two screws 16. The plate has a barrel 8 that holds the shaft 1 of the anchor bolt. A compression screw 14 is screwed into the threaded internal socket 3 of shaft 1. The head of the screw abuts the shoulder 15 of the barrel 8, so that when the compression screw is advanced into the shaft of the anchor bolt, the bolt will be drawn backwardly, reducing fracture 11a.

What is claimed is:

1. An anchor bolt for osteosynthesis having a cylindrical shaft with front and back ends, an external thread on said front end and an internally threaded socket at the back end, the major diameter of said external thread being greater than the diameter of the shaft, the thread profile of said external thread being of buttress configuration with the forward-facing flanks substantially perpendicular to the bolt axis, thereby enhancing resistance to forces acting from the front of the bolt.

2. Anchor bolt according to claim 1, characterized in that the backward-facing flanks of the external thread are positioned at an angle of between about 50° and about 60° to the bolt axis.

3. Anchor bolt according to claim 1, characterized in that the crests of the external thread have a blunted area, between about 0.5 and about 1.0 mm wide.

4. Anchor bolt according to claim 1, characterized by the fact that the external thread is a modified trapezoidal thread.

5. In a fixation device for treatment of a fractured bone comprising an anchor bolt having a cylindrical shaft with front and back ends, said shaft being an internally threaded socket at the back end and an external thread with a major diameter greater than the shaft diameter at the front end, a plate having means for attachment to the bone and a barrel adapted to fit over the shaft of the bolt, and a compression screw adapted to engage the internal threads of the socket, the improvement which comprises providing said external thread with a buttress configuration the forward flank of the external thread being substantially perpendicular to the axis of the bolt, thereby enhancing resistance to forces acting from the front of the bolt.

6. The device claimed in claim 5, wherein the rear flank of the external thread is inclined to the axis of the bolt at an angle of between about 50° and about 60°.

7. The device claimed in claim 5 wherein the crest of the external thread is blunted.

8. Anchor bolt according to claim 1 wherein the crests of the external thread are blunted.

* * * * *

UNITED STATES PATENT AND TRADEMARK OFFICE
CERTIFICATE OF CORRECTION

PATENT NO. : 5,116,336
DATED : May 26, 1992
INVENTOR(S) : Robert Frigg It is certified that error appears in the above-identified patent and that said Letters Patent is hereby corrected as shown below:

Col. 1, lines 26 & 27, delete sentence "In the profession, these devices are known as dynamic hip screws."

Signed and Sealed this

Third Day of August, 1993

Attest:

MICHAEL K. KIRK

*Attesting Officer*          Acting Commissioner of Patents and Trademarks